— US005811101A

United States Patent [19]

Waltman

[11] Patent Number: 5,811,101
[45] Date of Patent: Sep. 22, 1998

[54] COMPOSITION FOR TREATING ACNE

[75] Inventor: Herschel Waltman, Jackson, Miss.

[73] Assignee: Waltman Pharmaceuticals Incorporated, Jackson, Miss.

[21] Appl. No.: 841,052

[22] Filed: Apr. 29, 1997

[51] Int. Cl.⁶ ..................................................... A01N 65/00
[52] U.S. Cl. ........................ 424/195.1; 424/401; 514/859; 514/863; 514/886; 514/887
[58] Field of Search ................................. 424/401, 195.1; 514/859, 863, 886, 887

[56] References Cited

U.S. PATENT DOCUMENTS 5,470,579  11/1995  Bonte et al. .
5,658,581  8/1997  De Lacharriere et al. .

*Primary Examiner*—Thurman K. Page
*Assistant Examiner*—Brian K. Seidleck
*Attorney, Agent, or Firm*—John Lezdey

[57] ABSTRACT

A composition for treating acne and related skin conditions which contains salicylic acid and aloe vera which is improved by the addition of an effective amount of a methylxanthine. Preferably, the methylxanthine is derived from mate extract. A method for treating acne with the composition is also provided.

16 Claims, No Drawings

COMPOSITION FOR TREATING ACNE

FIELD OF INVENTION

The present invention relates to improved topical compositions for treating acne, psoriasis and acne related skin conditions. More particularly, there is provided a composition for treating acne which contains salicylic acid, aloe vera and a methylxanthine.

BACKGROUND OF THE INVENTION

Salicylic acid has been employed in the treatment of acne and related skin conditions for over sixty years. It is classified by the U.S. Food and Drug Administration as a Category I "safe and effective" non-prescription drug for the topical treatment of acne and related seborrheic conditions. However, because salicylic acid has a tendency to cause irritation, the over-the-counter (OTC) concentration is limited to about 2% by weight. Even at a concentration of 2%, salicylic acid can cause irritation, dryness and erythema of the skin.

Aloe vera has been used in the treatment of skin irritations and has been combined with salicylic acid for the treatment of acne. However, Aloe vera alone has only slightly reduced the irritation resulting from the use of salicylic acid. The combination of salicylic acid and aloe vera has still not resulted in the ability to use a salicylic acid concentration greater than two percent (2%).

SUMMARY OF THE INVENTION

The present invention provides a composition for the treatment of acne, psoriasis and acne related skin diseases with salicylic acid wherein there is a reduction in skin irritation. The composition comprises:

a) about 0.25 to 6.5% by weight of salicylic acid;

b) up to about 10% by weight of aloe vera, and c) an effective amount of a methylxanthine to reduce the skin irritation resulting from the salicylic acid.

Advantageously, the methylxanthine is derived from Mate extract.

The composition can be in the form of a suspension, cream, gel, lotion or shampoo.

The term "salicylic acid" as used herein is intended to mean salicylic acid and its derivatives, which are useful in the treatment of acne.

DESCRIPTION OF THE PREFERRED EMBODIMENTS

According to the present invention, there is provided a composition and method for the topical treatment of acne and related skin diseases such as seborrheic conditions which delivers a safe and effective amount of salicylic acid to the skin. The composition contains an effective amount of aloe vera and a methylxanthine, particularly derived as an extract from Paraguay tea, to form a synergistic combination to reduce visible and tactile irritation associated with salicylic acid.

The compositions of the invention comprise an effective amount of salicylic acid to treat acne. An effective amount is herein defined as the lowest concentration approved for an OTC drug by the FDA for the treatment of acne, which is 0.5 to 6% by weight.

The composition of the invention may contain chelating agents, such as EDTA and/or its salts and derivatives, or any other common chelating agent to prevent salicylic acid interaction or discoloration by trace metals.

Methylxanthines are found in Paraguay Tea and are available in an extract form known as "Mate extract". Mate extract is described in the "International Cosmetic Ingredient Dictionary", 5th Edition (1993). Mate extract is also commercially available in a combination with Kola and Guarana sold under the trademark "QUENCHT" by Cosmetic Ingredient Resources of Stamford, Conn. The combination provides a source of methylxanthines, saponins, flavonoids, tannins and glycosides which reduce swelling and redness associated with chemical irritations. The individual components are also commercially available. The Mate extract is used in an amount of about 0.1 to 7.0% by weight of composition. However, methylxanthines alone or when found in Mate extract is not sufficient to reduce the irritation by salicylic acid. Aloe vera has been found to be helpful to reduce some of this inflammation. Aloe vera is preferably used in an amount of about 0.25 to 10% by weight, most preferably about 0.25 to 2.0% by weight in combination with the methylxanthines but preferably with Mate extract. About 0.1 to 20% by weight of methylxanthines are used with the aloe vera to allow use of about 6.5% by weight salicylic acid. However, when the methylxanthine is in the form of mate extract, the Mate extract is used in an amount of about 0.1 to 7.0% as a result of the presence of other ingredients.

It is understood that while the present compositions preferably contain the combination of aloe vera and Mate extract, Mate extract can be used without aloe vera and still provide a reduction of irritation. Mate extract can be effective as aloe vera alone with a 2.0% by weight formation of salicylic acid. However, there is found to be a synergism when the combination of aloe vera and Mate extract is used so as to permit a greater concentration of salicylic acid.

The following examples illustrating the compositions of the invention are not intended to limit the scope of the invention. The amounts indicated are in percent by weight of composition.

EXAMPLE 1

A gel is prepared by admixing the following ingredients:

| | Ingredient | Wt % |
|---|---|---|
| 1. | Propylene Glycol | 51.94 |
| 2. | Carbomer 940 | 2.10 |
| 3. | Dipropylene glycol | 10.00 |
| 4. | Xanthan gum | 0.15 |
| 5. | Ethoxydiglycol | 15.00 |
| 6. | Dimethylisosorbide | 10.00 |
| 7. | Salicylic Acid | 2.00 |
| 8. | Chloroxylenol | 0.20 |
| 9. | Linoleamidopropyl PG-diammonium chloride phosphate | 1.50 |
| 10. | Glycereth 4.5 Lactate | 2.00 |
| 11. | Aloe Vera Gel | 2.00 |
| 12. | Kola (and) Guarana (and) Mate Extract | 2.00 |
| 13. | Tetrasodium EDTA | 0.10 |
| 14. | Citric Acid | 0.010 |
| 15. | Cocamidopropyl PG-dimonium chloride phosphate | 1.00 |

Ingredients 1 and 2 are mixed to disperse and form a gel. About 80% of ingredient 3 is mixed with ingredient 4, added to the gel and heated with mixture to 47 degrees C. The balance of 3 is mixed with ingredients 5–10 and added to the gel. Ingredients 11–15 are then admixed and added to the gel at 38 degrees C. After mixing, the gel is brought to room temperature.

EXAMPLE 2

A lotion is prepared by admixing the following ingredients:

| Ingredient | Wt % |
|---|---|
| Propylene Glycol Stearate | 6.50 |
| Isocetyl alcohol | 5.00 |
| PEG-100 Stearate | 1.20 |
| Water | 69.90 |
| Disodium EDTA | 0.10 |
| Methyl paraben | 0.20 |
| Propylene glycol | 12.00 |
| Sorbitan palmitate | 0.60 |
| Salicylic Acid | 2.00 |
| Aloe Vera gel | 2.00 |
| Mate extract | 0.50 |
| | 100% |

EXAMPLE 3

A cream is prepared by mixing the following ingredients:

| Ingredient | Wt % |
|---|---|
| Glyceryl stearate | 11.0 |
| PEG-100 stearate | 2.0 |
| Cetostearyl alcohol | 2.5 |
| Disodium EDTA | 0.1 |
| Methyl Paraben | 0.1 |
| Propylene glycol | 11.0 |
| Sorbitan stearate | 0.7 |
| Salicylic acid | 2.0 |
| Aloe vera gel | 2.0 |
| Mate extract | 0.5 |
| Water | 8.5 |
| | 100% |

EXAMPLE 4

A gel is prepared by admixing the following ingredients:

| Ingredient | Wt % |
|---|---|
| Carbomer | 2.80 |
| Propylene Glycol | 92.05 |
| Disodium EDTA | 1.10 |
| Methyl Paraben | 0.20 |
| Salicylic Acid | 2.00 |
| Mate extract | 0.35 |
| Aloe Vera Gel | 2.50 |
| | 100% |

EXAMPLE 5

A solution according to the invention is prepared by admixing the following ingredients:

| Ingredient | Wt % |
|---|---|
| Ethoxyglycol | 15.00 |
| Propylene Glycol | 35.00 |
| Ethanol | 25.00 |
| Water | q.s. |
| Disodium EDTA | 0.10 |
| Salicylic Acid | 2.00 |
| Mate Extract | 2.50 |
| Aloe Vera Gel | 1.75 |
| | 100% |

EXAMPLE 6

A shampoo is prepared by admixing the following ingredients:

| Ingredient | Wt % |
|---|---|
| C12–15 Pareth-7 Carboxylic Acid | 10.0 |
| Isosteareth-6 Carboxylic Acid | 5.0 |
| Hexylene Glycol | 8.0 |
| Chloroxylenol | 0.5 |
| Salicylic Acid | 2.0 |
| Mate Extract | 0.5 |
| Aloe Vera Gel | 2.0 |
| Na2 EDTA | 0.1 |
| Water | 71.9 |

EXAMPLE 7

Comparison Studies

I. Human Clinical Study

Commercially available salicylic acid topical medications are available in the U.S. without prescription, containing up to 2% salicylic acid, for the treatment of acne. These preparations are known to cause undesirable side effects such as mild burning, irritation, redness and skin dryness. The composition of this invention, containing aloe vera gel and Mate was compared in a clinical acne study with a nationally available salicylic acid (2%) topical that does not contain aloe vera gel or Mate extract (Johnson and Johnson's "Clean & Clear" . . . "Invisible Blemish Treatment". Both preparations were equivalent in overall efficacy, but the subject composition provided a greater rate of positive response with less local side effects, particularly less skin reddening and/or skin dryness/irritation.

II. Animal Safety (Dermal) Tests

A. Using guinea pigs, a topical application of salicylic acid 6% containing the composition of this patent application was compared with salicylic acid 2% in the same vehicle, but without aloe vera gel and Mate extract. The 6% salicylic acid composition of the instant invention was either equal to or less irritating than the 2% salicylic acid preparation, in every subject animal, following ten (10) consecutive days of repeat insult patch testing.

B. A second repeat insult patch test series was run on guinea pigs divided into thee groups: Group one (1) received salicylic acid topical gel, 2%, with 10% aloe vera gel; group two (2) received salicylic acid topical gel, 2% with Mate extract 5%; group three (3) received salicylic acid topical gel, 2%, of the instant invention [i.e., with 2% aloe vera gel and 0.5% Mate extract]. In each instance the salicylic composition [Group 3] was less drying and irritating than either Group 2 or Group 1.

What is claimed is:

1. A topical composition for the treatment of acne, and psoriasis which comprises:

a) about 0.25 to 6.5% by weight of salicylic acid;

b) up to about 10% by weight of aloe vera, and c) an effective amount of a methylxanthine to reduce the skin irritation resulting from salicyclic acid.

2. The composition of claim 1 comprising about 0.25 to 2% by weight of salicylic acid.

3. The composition of claim 1 comprising about 0.5 to 2% by weight of aloe vera.

4. The composition of claim 1 comprising about 0.1 to 20% by weight of methylxanthine.

5. The composition of claim 1 wherein said methylxanthine is an extract of Paraguay Tea.

6. The composition of claim 5 wherein said extract is Mate extract.

7. The composition of claim 1 wherein said Mate extract is in an amount of about 0.1 to about 7.0% by weight.

8. The composition of claim 1 including an extract selected from the group consisting of Kola and Guarana.

9. The composition of claim 1 including an effective amount of saponin, flavonoid, tannin and glycoside to reduce swelling and redness.

10. A composition for the topical treatment of acne and psoriasis which comprises
    a) about 0.25 to 6.5% by weight of salicylic acid;
    b) about 0.25 to 10% by weight of aloe vera, and
    c) an effective amount of Mate extract to reduce erythema.

11. The composition of claim 10 which is a gel.

12. The composition of claim 10 including Kola and Guarana extract.

13. A method for the treatment of acne and psoriasis which comprises topically administrating to the site of said acne and psoriasis an effective amount of the composition of claim 1.

14. A method for the treatment of acne and psoriasis which comprises topically administrating to the site of said acne and psoriasis an effective amount of the composition of claim 5.

15. A method for the treatment of acne and psoriasis which comprises topically administrating to the site of said acne and psoriasis an effective amount of the composition of claim 10.

16. A method for the treatment of acne and psoriasis which comprises topically administrating to the site of said acne and psoriasis an effective amount of the composition of claim 11.

* * * * *